US011027092B2

(12) United States Patent
Bode

(10) Patent No.: US 11,027,092 B2
(45) Date of Patent: Jun. 8, 2021

(54) SYSTEM AND METHODS FOR DESIGN, OPERATION AND USE OF THE MAGNETIC RESONANCE OF THE EARTH FOR SLEEP ENHANCEMENT

(71) Applicant: Serenity Wave, LLC, Fort Smith, AR (US)

(72) Inventor: Paul M. Bode, Fort Smith, AR (US)

(*) Notice: Subject to any disclaimer, the term of this patent is extended or adjusted under 35 U.S.C. 154(b) by 342 days.

(21) Appl. No.: 15/833,268

(22) Filed: Dec. 6, 2017

(65) Prior Publication Data

US 2018/0154105 A1  Jun. 7, 2018

Related U.S. Application Data

(60) Provisional application No. 62/431,023, filed on Dec. 7, 2016.

(51) Int. Cl.
*A61M 21/02* (2006.01)
*A61N 2/02* (2006.01)
*A61N 2/00* (2006.01)
*A61M 21/00* (2006.01)

(52) U.S. Cl.
CPC ............ *A61M 21/02* (2013.01); *A61N 2/02* (2013.01); *A61M 2021/0055* (2013.01); *A61M 2205/8262* (2013.01); *A61N 2/006* (2013.01)

(58) Field of Classification Search
CPC .......... A61M 21/02; A61M 2021/0055; A61M 2205/8262; A61N 2/02; A61N 2/006
USPC ....................................................... 600/9–15
See application file for complete search history.

(56) References Cited

U.S. PATENT DOCUMENTS

| | | | |
|---|---|---|---|
| 4,723,536 A | 2/1988 | Rauscher et al. | |
| 5,620,463 A * | 4/1997 | Drolet | A61N 2/02 607/3 |
| 5,935,054 A * | 8/1999 | Loos | A61N 2/02 600/9 |
| 6,004,257 A | 12/1999 | Jacobson | |
| 6,203,486 B1 * | 3/2001 | Miller | A61N 2/02 600/9 |
| 7,326,170 B1 * | 2/2008 | Miller | A61N 2/02 600/9 |
| 7,819,794 B2 | 10/2010 | Becker | |
| 8,517,909 B2 | 8/2013 | Honeycutt et al. | |
| 9,649,502 B2 | 5/2017 | Philips et al. | |
| 10,500,408 B2 | 12/2019 | Helekar et al. | |

(Continued)

OTHER PUBLICATIONS

Design of Miniature Coil to Generate Uniform Magnetic Field. Nilangshu K. Das, Parthasarathi Barat, Sounak Dey, and Tammana Jayakumar. Progress In Electromagnetics Research M, vol. 34, 99-105, 2014 (Year: 2014).*

*Primary Examiner* — Navin Natnithithadha
*Assistant Examiner* — Sunita Reddy
(74) *Attorney, Agent, or Firm* — The Roy Gross Law Firm, LLC; Roy Gross

(57) ABSTRACT

A device for replicating a natural magnetic vibration of Earth, promoting more restful sleep. The device produces an appropriately uniform magnetic field across the surface of the area where the head rests during sleep. The device provides a varying magnetic field therapy that allows a user to sleep in their usual manner using their existing familiar pillow, with no changes to the aesthetics of the bed, while using the device having varying magnetic field therapy capabilities.

12 Claims, 10 Drawing Sheets

(56) References Cited

U.S. PATENT DOCUMENTS

| | | | | |
|---|---|---|---|---|
| 2003/0045770 | A1* | 3/2003 | van Mullekom | A61N 2/02 600/9 |
| 2004/0077921 | A1* | 4/2004 | Becker | A61N 2/008 600/9 |
| 2004/0102673 | A1* | 5/2004 | Baugh | A61N 2/02 600/9 |
| 2005/0027158 | A1* | 2/2005 | Becker | A61N 2/008 600/9 |
| 2005/0182287 | A1* | 8/2005 | Becker | A61N 2/008 600/13 |
| 2007/0293916 | A1* | 12/2007 | Peterchev | A61N 2/02 607/61 |
| 2011/0301402 | A1* | 12/2011 | Xu | A61N 2/006 600/14 |
| 2012/0053394 | A1* | 3/2012 | Honeycutt | A61N 2/02 600/27 |
| 2012/0109241 | A1* | 5/2012 | Rauscher | A61B 5/40 607/9 |
| 2013/0137918 | A1* | 5/2013 | Phillips | A61N 2/02 600/14 |
| 2015/0140633 | A1* | 5/2015 | Vladila | A01G 7/04 435/173.8 |
| 2015/0150653 | A1* | 6/2015 | Vladila | A61K 6/69 433/29 |
| 2015/0297910 | A1* | 10/2015 | Dimino | A61N 2/02 600/14 |
| 2015/0314133 | A1* | 11/2015 | Yamashiro | A61N 2/006 600/14 |
| 2018/0126185 | A1* | 5/2018 | Hochstenbach | A61N 2/02 |

* cited by examiner

Figure 1
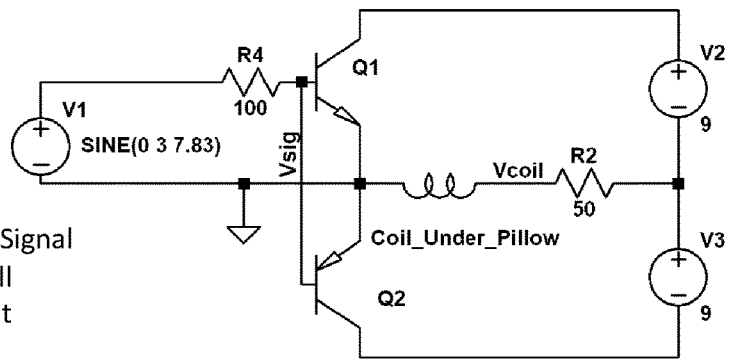
First embodiment of circuit: Signal generator feeding a push-pull circuit powered by two 9-volt batteries.
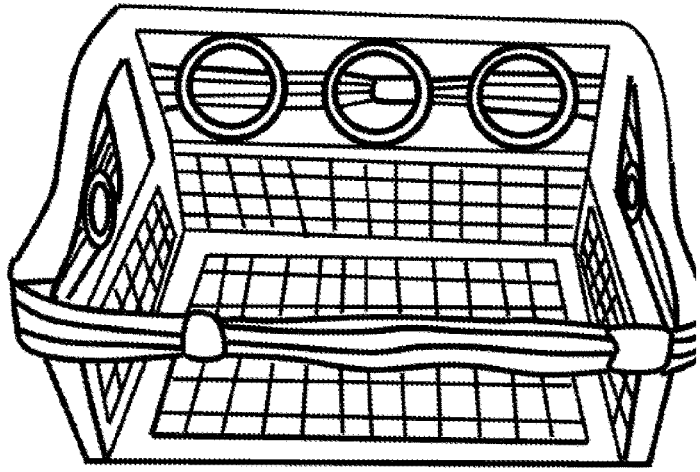
First embodiment of coil: Approximately 80 turns of stranded insulted wire wound with a circumference of approximately 42 inches.
Signal Input and Coil current.
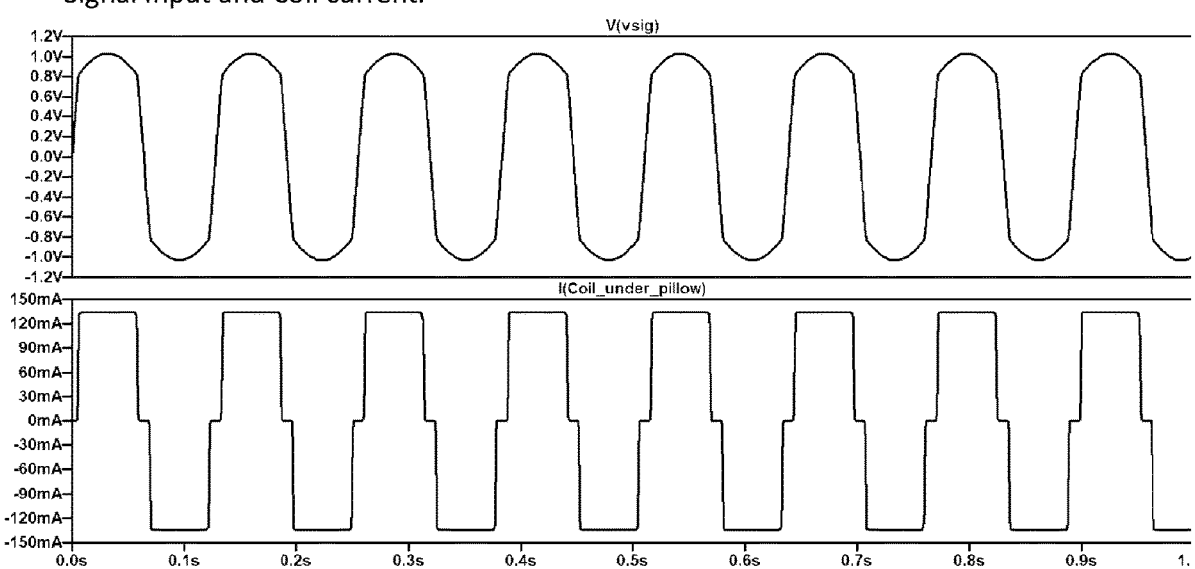

Figure 2
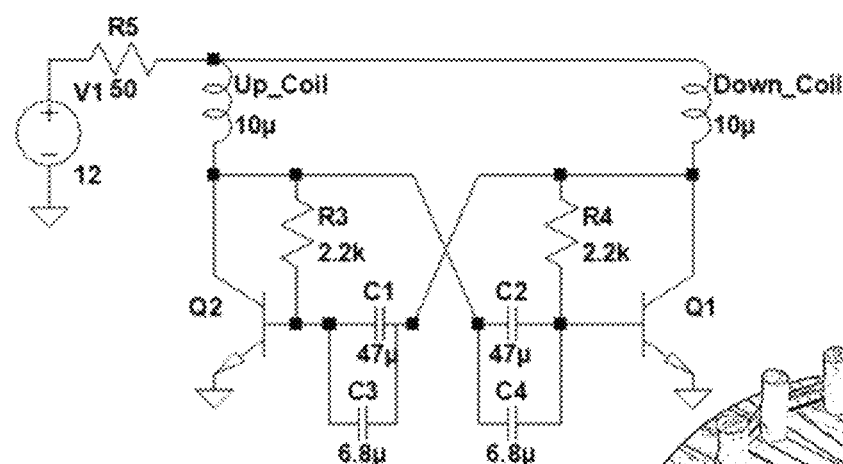
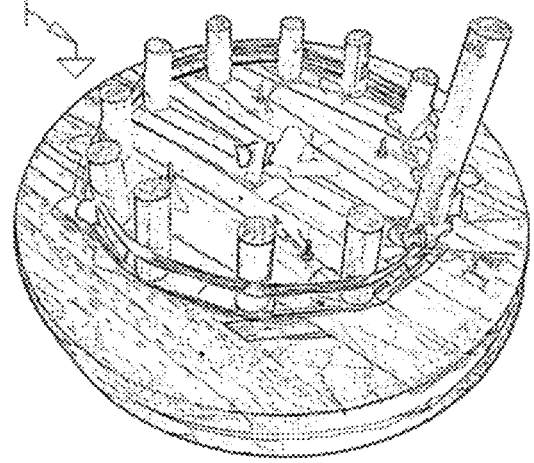
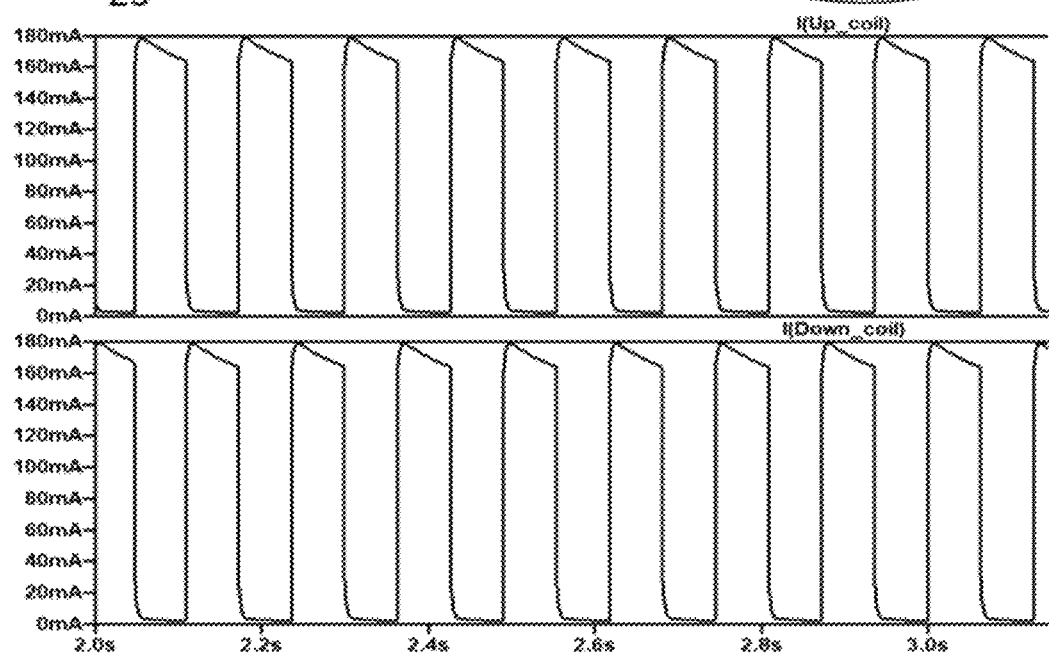

Figure 3
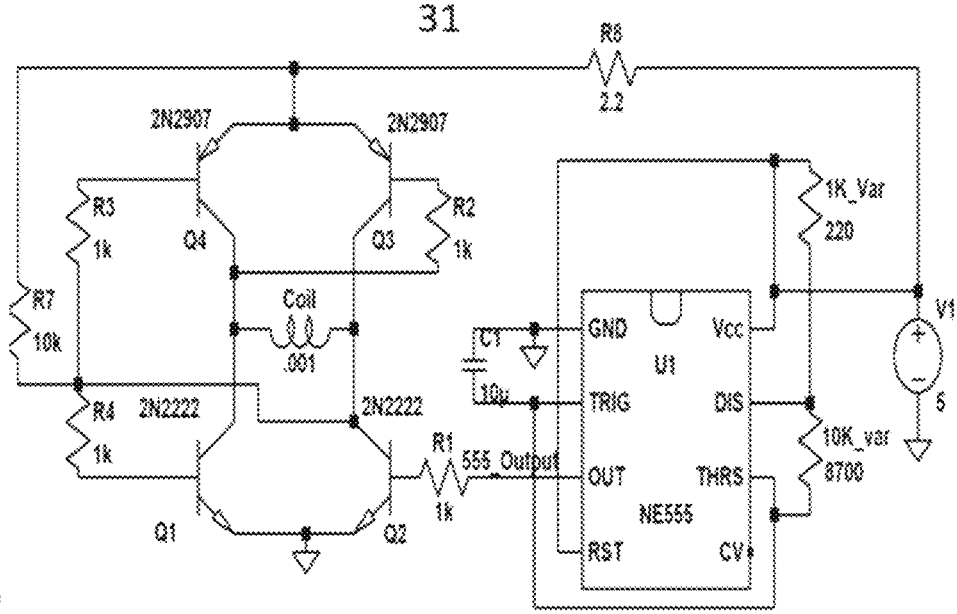
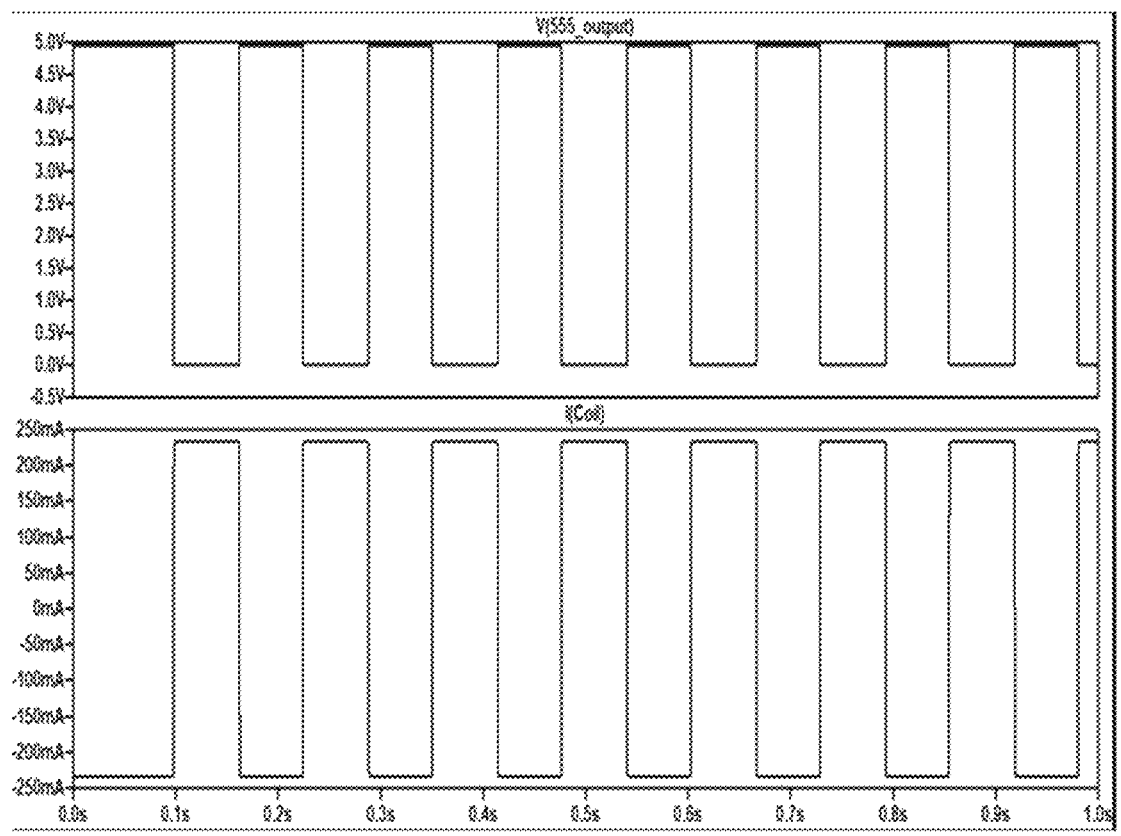

Figure 4
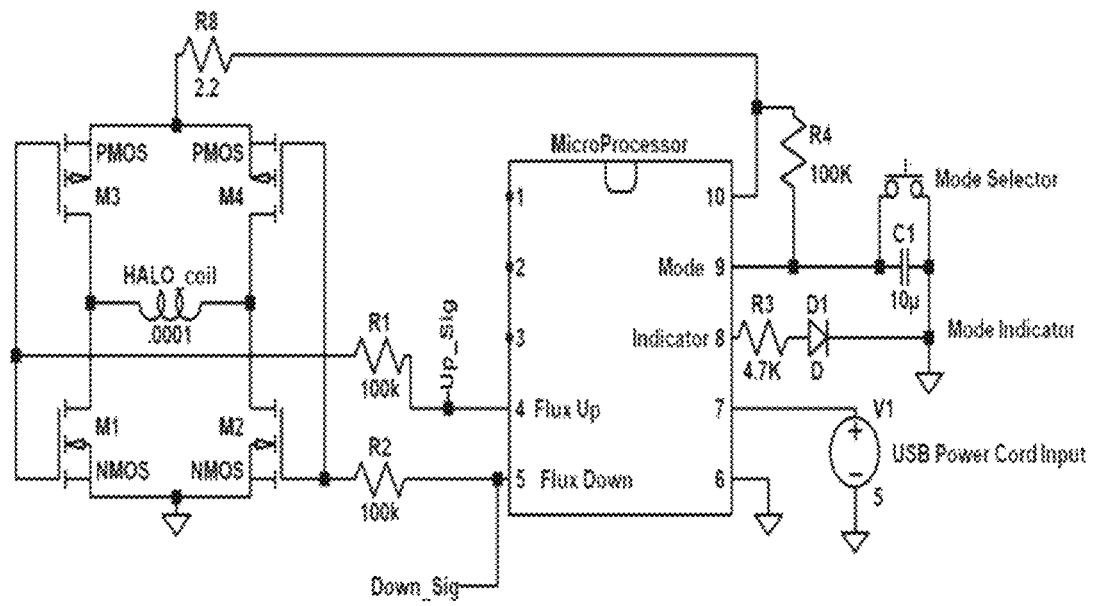
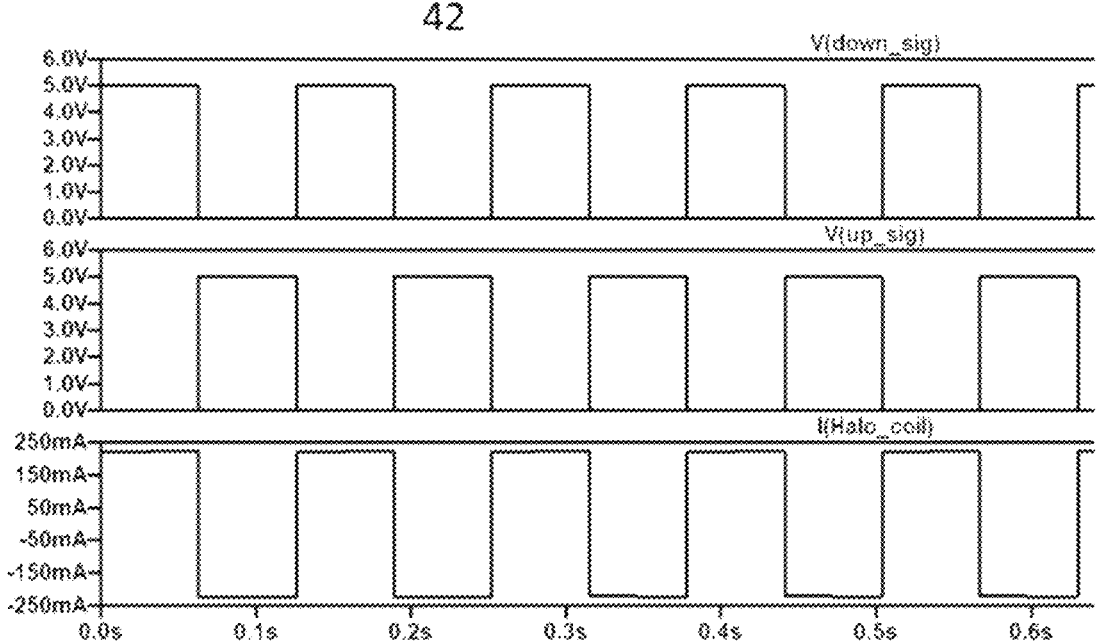

Figure 5
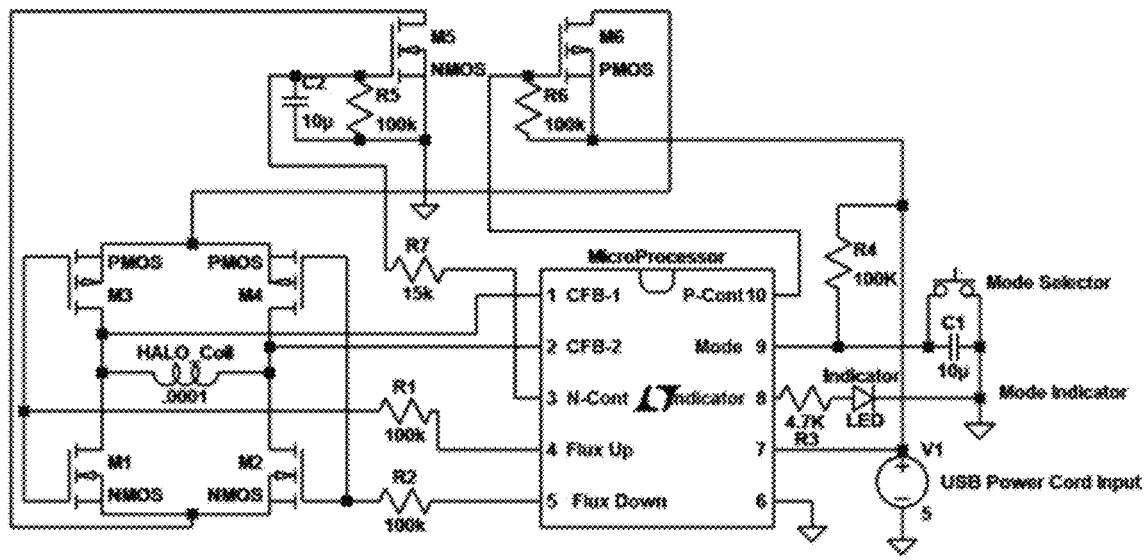
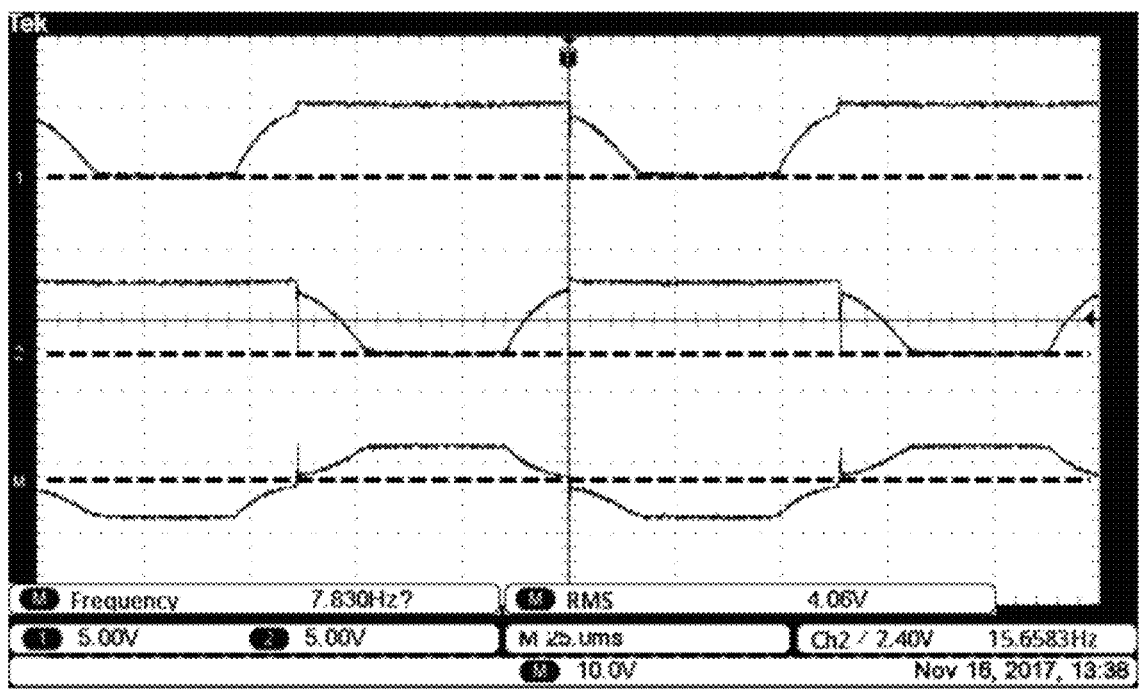

Figure 7
Typical Embodiment of Human Proportions

Head Dimensions
Source: NASA-STD-3000, the Man-System Integration Standards

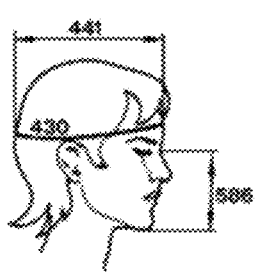

Female

| No. | Dimension | 5th percentile | 50th percentile | 95th percentile |
|---|---|---|---|---|
| 441 | Head length | 16.7 (6.6) | 18.2 (7.2) | 19.6 (7.7) |
| 430 | Head circumference | 53.2 (20.9) | 55.2 (21.7) | 57.2 (22.5) |
| 165 | Bizgomatic (face) breadth | 13.3 (5.2) | 14.5 (5.7) | 15.7 (6.2) |
| 427 | Head breadth | 14.4 (5.7) | 15.6 (6.1) | 16.8 (6.6) |

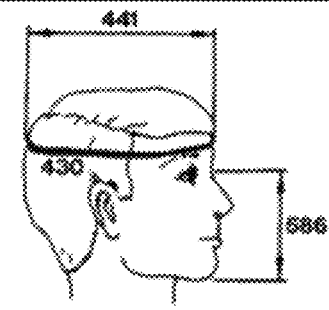

Male

| No. | Dimension | 5th percentile | 50th percentile | 95th percentile |
|---|---|---|---|---|
| 165 | Bizgomatic (face) breadth | 13.4 (5.3) | 14.3 (5.6) | 15.1 (6.0) |
| 427 | Head breadth | 14.8 (5.8) | 15.7 (6.2) | 16.5 (6.5) |
| 441 | Head length | 18.8 (7.4) | 20.0 (7.9) | 21.1 (8.3) |
| 430 | Head circumference | 55.5 (21.8) | 57.8 (22.8) | 60.2 (23.7) |

Values in cm with inches in parentheses

Typical Gauss Developed By Coil, Placed Top/Bottom of Pillow

SYSTEM AND METHODS FOR DESIGN, OPERATION AND USE OF THE MAGNETIC RESONANCE OF THE EARTH FOR SLEEP ENHANCEMENT

CROSS-REFERENCE TO RELATED APPLICATION

This application claims the benefit of U.S. Provisional Application No. 62/431,023 entitled "Serenity Wave", filed Dec. 7, 2016. The foregoing application is incorporated herein by reference in its entirety.

BACKGROUND OF THE INVENTION

The use of varying magnetic field therapy devices has been acknowledged by the current medical industry in the United States as being beneficial in specific healing situations.

However, none of the cited art is directed to a varying magnetic field therapy device that allows a user to sleep in their usual manner using their existing familiar pillow, with no changes to the aesthetics of the bed, while using a device having varying magnetic field therapy capabilities.

Existing systems include:

| Pat. No. | Kind Code | Issue Date | Patentee | Title |
| --- | --- | --- | --- | --- |
| 9,649,502 | B2 | May 16, 2017 | James Phillips Yi Jin | Devices and methods of low frequency magnetic stimulation therapy |
| 8,517,909 | B2 | Aug. 27, 2013 | James Honeycutt John Honeycutt | Apparatus and methods to improve sleep, reduce pain and promote natural healing |
| 6,203,486 | B1 | Mar. 20, 2001 | Wendell Miller Robert South Michael South | Earth magnetic-field augmenters |
| 7,819,794 | B2 | Oct. 26, 2010 | Paul Becker | Method and apparatus for the treatment of physical and mental disorders with low frequency, low flux density magnetic fields |
| 6,004,257 | N/A | Dec. 21, 1999 | Jerry Jacobson | Method for ameliorating the aging process and the effects thereof utilizing electromagnetic energy |
| 4,723,536 | N/A | Feb. 9, 1988 | Elizabeth Rauscher William Van Bise | External magnetic field impulse pacemaker non-invasive method and apparatus for modulating brain through an external magnetic field to pace the heart and reduce pain |

U.S. Pat. No. 6,203,486 claims to augment the Earth's magnetic field but does so in a static manner, exceeding the strength of what naturally occurs.

U.S. Pat. No. 8,517,909 is a complex device that requires many steps to set up and operate and exposes other people in the bed to the magnetic field over the length of their body, and requires the use of specific technology in terms of a Fibonacci quartz crystal.

U.S. Pat. No. 9,649,502 requires a device to be placed on a head of a user and would be uncomfortable to sleep with.

None of the cited art suitable for use in a bed while sleeping provides a method and system having no head bands, no electrodes taped to the user, no matts to sleep on, no therapeutic lights, and no therapeutic sounds.

It is an object of the present invention to overcome the disadvantages of the cited art and to provide a varying magnetic field therapy device that allows for a user to sleep in a normal manner while using the device.

SUMMARY OF THE INVENTION

It is an object of the invention to provide a dynamic, low-level magnetic field to a user while the user is sleeping, emulating a natural resonance of the Earth.

It is an object of the invention to provide a magnetic field to a single user having negligible impact on others in the same bed or the same room.

It is an object of the invention to provide a single magnetic field to a single user in the vicinity of a head of the user at any given time during use.

It an object of the invention to provide a uniform flux through the entire head of a user using a magnetic field.

These and other objects of the invention are achieved by providing a varying magnetic field generating system comprising: a current-conducting coil configured to create a varying magnetic field in the vicinity of the head of the user while the user is sleeping; and an electronic module to power the coil at a low frequency less than or equal to 8 Hz.

In certain embodiments, the coil is comprised of magnet wire.

In certain embodiments, the coils are flexible or rigid coils.

In certain embodiments, the coil is circular or substantially circular.

In certain embodiments, the coil has a cover, typically a flexible helical cover or flexible over-mold.

In certain embodiments, the coil is directly and permanently connected to the electronic module.

In certain embodiments, the coil is plugged into the electronic module enclosure via a cable.

In certain embodiments, a standard micro-USB cable plugs into the other side of the electronic module to power the unit from any USB type 'A' female jack.

In certain embodiments, an indicator ring is provided that indicates whether the magnetic field generating system is functioning properly and/or is producing a magnetic field.

In certain embodiments, a push button is provided that is used to energize or de-energize the coil if desired.

In certain embodiments, pressing the push button is not required to operate the unit.

In certain embodiments, the diameter of the coil is larger than a human head in any cross-section.

In certain embodiments, the system produces a low-gauss variance in the magnetic field in the area of the head.

In certain embodiments, an amplitude in the gauss variance across the head of the user averages between 0 and 1 Gauss.

In certain embodiments, the coil is configured to be inserted into a pillow case of the user or beneath a pillow of the user, or behind the headboard in the vicinity of the head of the user.

In certain embodiments, the electronic module is devoid of specific or special crystal or crystals.

In certain embodiments, the system enhances sleep exclusively with the application of the varying magnetic field without the use of any other therapeutic means.

In certain embodiments, the magnetic field varies at a single frequency.

In certain embodiments, the system defaults to a single frequency of 7.83 Hz.

In certain embodiments, the system defaults to a frequency within the range of human brain waves during sleep, which is also a frequency of a natural magnetic resonance of the Earth.

In certain embodiments, the electronic module is configured to operate on <500 mA at 5V.

In certain embodiments, the system uses an astable multivibrator.

In certain embodiments, the electronic module is configured to be powered using any standard USB port or power supply.

In certain embodiments, the system is devoid of any smart phone, tablet or personal computer.

In certain embodiments, the system is configured to work without direct contact of any of its components with the user, and wherein the system is devoid of head-bands, electrodes or other such devices placed on or attached to the body, while the user is sleeping.

In certain embodiments, the system is configured to be operated automatically without user control.

In certain embodiments, the system is configured to produce a natural gentle magnetic field.

Other objects of the invention are achieved by providing a method of assisting a user to sleep, the method comprising: providing a low-gauss, low-frequency magnetic field to the user, thereby promoting sleeping and enhancing the quality of sleep.

In certain embodiments, the low-gauss, low-frequency magnetic field is generated as a wave.

In certain embodiments, the low-gauss, low-frequency magnetic field is applied devoid of pulses.

In certain embodiments, the coil is placed around the head of the user.

In certain embodiments, the coil is placed in a pillow or below the pillow of the user.

In certain embodiments, the coil is placed behind the headboard in the area of the user.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The figures provided here show the progression of embodiments from conception and proof of concept, to commercial production.

FIG. 1 is directed to a schematic of a common-emitter class-A biased NPN transistor driven by a sine wave with a DC offset of 0.9 volts and an amplitude of 0.265 volts;

FIG. 2 is directed to an astable multivibrator approach to generating the magnetic flux.

FIG. 3 is directed to a 555-timer-driven approach and a transistorized H-bridge configuration for providing current to the coil.

FIG. 4 is directed to a micro-processor driven output to the h-bridge, and a shift from BJTs to MOSFETs.

FIG. 5 is directed to a schematic of a circuit with a microprocessor.

FIG. 7 is a chart showing female and male Man-System Integration Standards to provide a frame of reference for establishing the size of the coil and its magnetic strength.

DETAILED DESCRIPTION OF THE INVENTION

In the following description, numerous details are set forth for the purpose of explanation. However, one of ordinary skill in the art will realize that the invention may be practiced without the use of these specific details.

Figure 6:
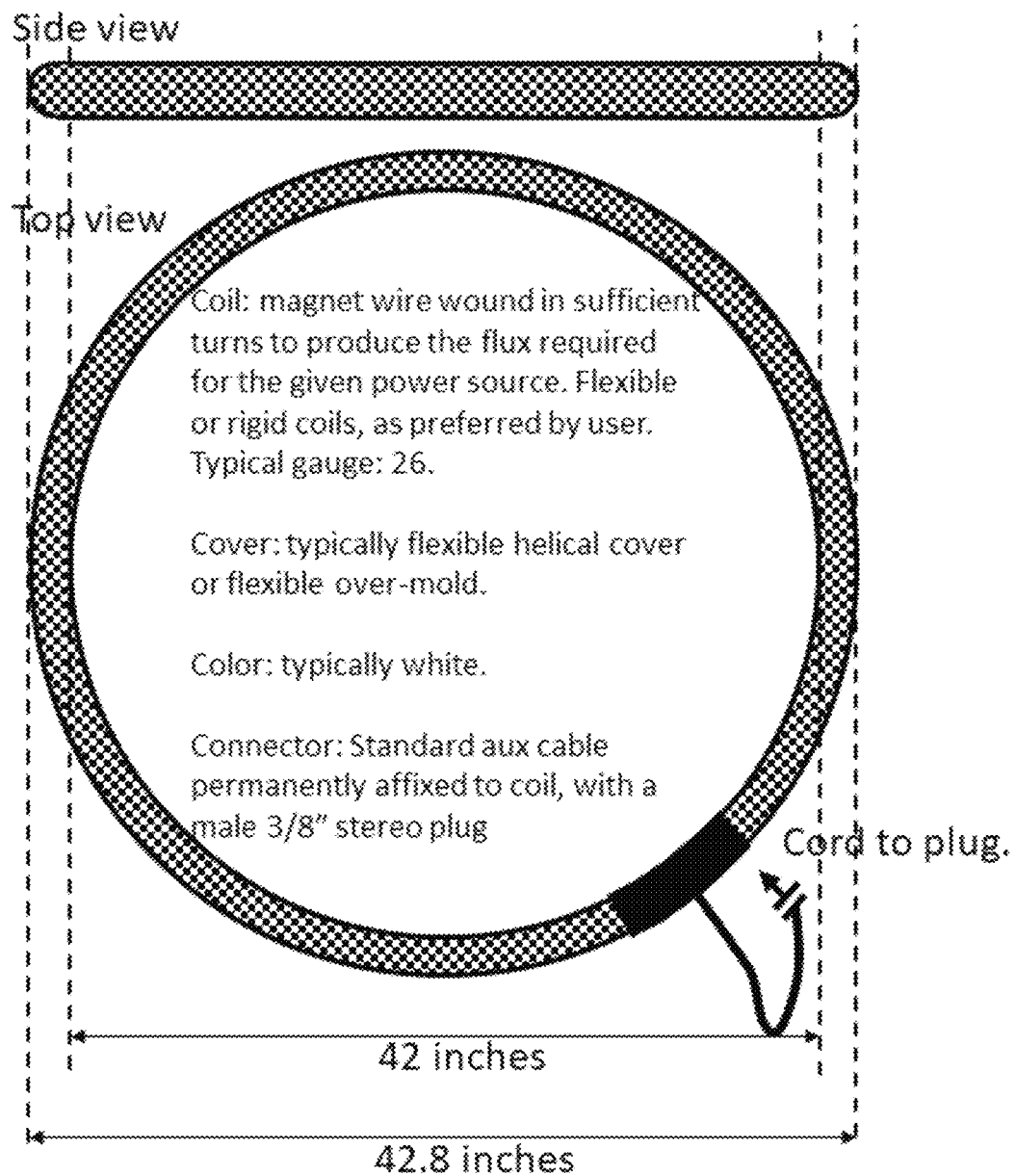
FIG. 6 is directed to an embodiment of the coil of an embodiment of the invention.

FIG. 6 shows an overview of the coil of an embodiment of the invention. The coil allows the user to sleep comfortably while enjoying the benefit of a steady magnetic resonance similar to what Earth produces at times. In certain embodiments, a user can insert the coil into his or her existing pillow so their sleep experience is relatively unchanged, physically and aesthetically.

Figure 8:
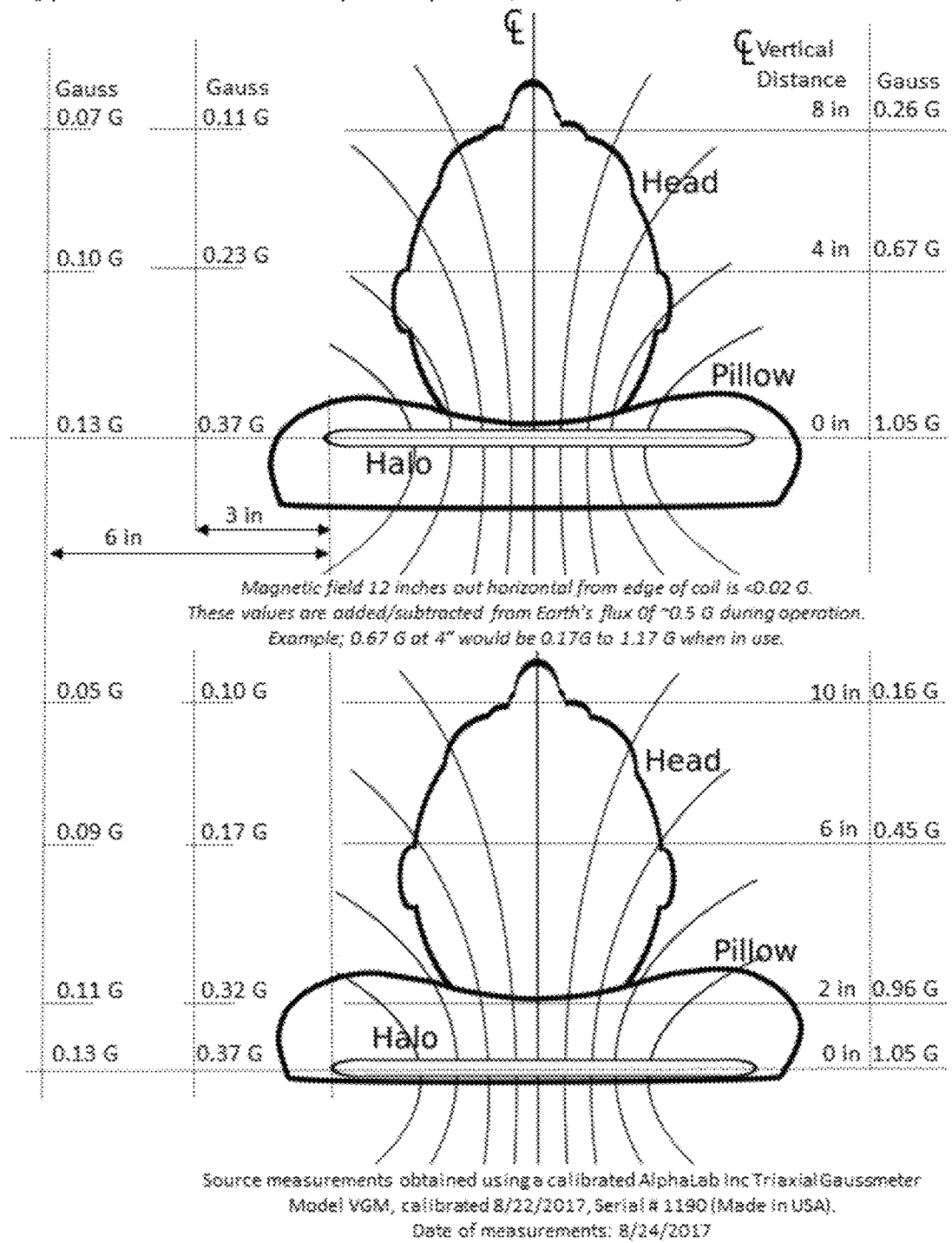
FIG. 8 is a typical propagation of magnetic flux vertically up through the center-line of the coil (right axis), and horizontally out from the side of the coil (left axis).

FIGS. 7 and 8 form the objective basis for establishing flux levels at various heights and distances from the pillow.

Experimental Research

The inventor desired to improve the quality of sleep for his wife because he noticed she was a fitful sleeper and also had grown dependent upon an electric fan near her while she slept. His background led him to understand the potential detrimental impact of a fan running continually close to her while she slept. His research into those effects led him to create this new device described herein.

During the inventor's research, he came across numerous medical experiments which showed that magnetic fields played an important role in health and well-being.

In one experiment, the simple removal of all magnetic fields, including the Earth's own magnetic field had repeatable, detrimental impact on test subjects. In other experiments, pulsed magnetic fields can stimulate repair of various types of tissues in the human body, and can influence the operation of the brain. In related research, the inventor came across a study of fear and stress and learned that the only two natural fears a baby is born with are fear of loud noises and fear of falling. In a flash of inspiration unexpectedly, the inventor came to the realization that in the past pre-technological eras, typically the only loud, frightening noise a person was subjected too was a clap of thunder or the voice of God. Preceding the clap of thunder would be a bolt of lightning (lightening being a phenomenon the inventor had previously studied with great interest for the purposes of capturing electrical energy).

In typical electrical storms, many bolts of lightning occur, cloud-to-cloud, and cloud to ground. Both mechanisms have powerful magnetic phenomenon associated with them, and this magnetic energy imparts energy to the Earth's magnetic field, pinging it like a huge bell. The inventor intrinsically understood that for a physical object, including cells within the brain, and molecules within those cells, to react to a force applied to it, a key component was not just the magnitude of the force, but its duration. In systems capable of mutual resonance, a weak force can transfer a lot more energy (via a wave) over time than a sharp burst (pulse) can. If a wave oscillates near a resonant frequency of an object exposed to it (kinetic, magnetic or electric waves), it can impart ever increasing amounts of energy via a wave. Whereas pulsed electromagnetic therapy (PEMT) typically requires stronger gauss levels to achieve effectiveness, a key objective of this invention is to achieve results overnight with a gentler, weaker wave whose strength is on the order of magnitude of the Earth's own natural magnetic field.

The inventor realized that the lightning bolts would transfer energy to the Earth's magnetic field. Those intermittent, brief magnetic pulses would have little effect on the brain's magnetic moment. However, the ensuing ripple on the Earth's magnetic field would have an effect as they would be sustained in duration at discrete frequencies. One of those frequencies, a main one, is in the range of sleep of human beings, and also in the range that increase production of hormones that promote calmness and physical well-being. In summary, the inventor understood that humans' brains and bodies appear to be intelligently designed to respond to a loud noise produced by nature, potentially frightening us, by calming us down via the ensuing ripples in the Earth's magnetic field. The inventor has measured these ripples directly. This confluence of knowledge of different areas of science were the impetus to explore restoring a naturally occurring magnetic resonance to the sleep cycle. By being exposed to a low-power magnetic wave of the frequency of the Earth's magnetic wave when impinged upon by magnetic fields of lightning bolts, for the duration of a sleep cycle, a user is essentially enjoying the geomagnetic results of a virtual lighting storm.

Consequently, the inventor developed a device that would allow a user to sleep on a relatively weak, 7.83 hertz magnetic field. The inventor wanted the strength of the varying field to be the approximate strength of Earth's magnetic field. The inventor wanted to stay around one Gauss or below, as the Earth's own strength is about 0.5 Gauss. Too weak was not good either.

The inventor then developed a device that would produce a gentle, natural magnetic field. The inventor developed a device to replicate Earth's natural magnetic resonance of 7.83 hertz, with no other complicating frequencies, at the approximate strength of the Earth's magnetic field.

The inventor discovered that a coil with a diameter that is larger than a human head produces a magnetic field that has a low gradient. In this manner, the gradient does not drop off quickly through a person's head and provides uniform flux through a user's head. In this manner, a natural magnetic field is provided that has positive therapeutic effects, especially upon the sleep of users.

In certain embodiments, the device uses a single frequency. In certain embodiments, the device does not affect the entire body and other people who may also be sleeping in the same bed. In certain embodiments, the device is easy to set up and use.

In certain embodiments, the device produces a magnetic field in a coil which is placed such that the flux from the coil permeates the head of the person using the coil. The flux alternates its direction through the coil at a default frequency of 7.83+/−0.02 hertz. The strength of the magnetic field is on the order of magnitude of Earth's magnetic field which is approximately 0.5 gauss. This is much less than some gauss strengths people expose themselves to while sleeping, often in the thousands of gauss range.

The inventor has found that replicating this natural magnetic resonance of Earth, continually, while a user sleeps, at a low safe level, on the order of magnitude of Earth's own magnetic field, in such a way as any user can use it and not be intimidated by complex controls or directions, is advantageous to encourage lay people to enjoy the benefits of this invention.

There currently is no device that does what this device does, how it does it. The inspiration, and the confluence of design, operation and use of the device is singularly unique. The device is so simple to use, people are expanding its use on their own. You simply place the coil in your pillow and plug it in. No need for adjustments. Nothing to wear, no headbands, no electrodes on the skin. No therapeutic sounds. No therapeutic lights.

As a result of his research, the inventor has helped many people already at the writing of this application, and has over one hundred units in service spread across nine states. The inventor has formed a company and his begun commercial manufacturing.

Advantages

The device demonstrably promotes sleep, and enhances the quality of sleep, silently, without the need to attach anything to the body of the user, take any medication, listen to any sounds, look at any lights or require you to sleep on anything that you don't already own and are happy with, and does this by emulating a natural magnetic resonance of the Earth.

The device uses a magnetic field strength far weaker (typically by thousands of Gauss) than most magnetic pillows people sleep on, and most PEMT devices.

Because it defaults to a natural frequency, a frequency the users know they are exposed to by Earth anyway, at a strength on the order of magnitude of the Earth's own magnetic field, users feel safe using the device on themselves, and their children and pets.

Because the device is so unobtrusive and easily placed, it lends itself to quick assimilation to everyday use, and also allows for expanded use with children, and even pets. As an example, for autistic children who require routine and consistency, the coil has been placed by their parents under the mattress sheet in the vicinity of where the head rests.

Because a user does not require a laptop, PC, tablet or cell phone to use the device, and a user is not even required to press any buttons or read anything on the device to make it work, even the most technologically challenged person can quickly and confidently use this device. This is a distinct advantage over other types of devices.

Because the unit was designed to be powered by an almost universally available USB power system, users have greater flexibility for powering their devices than any previous device. Almost everyone has USB chargers these days.

It does not require complex construction, circuitry or any special crystals, allowing it to reach more people as it costs significantly less than most devices using varying magnetic fields.

+/−20% to +/−5% from marked values. The figures herein show typical values, and where applicable, typical dimensions for the embodiment being represented in the figure.

FIG. 1, reference number 11 shows a schematic of a common-emitter class-A biased NPN transistor driven by a sine wave with a DC offset of 0.9 volts and an amplitude of 0.265 volts. FIG. 1, reference number 12 shows a coil wound on a rectangular frame. The coil was used in that shape as well as oval and circular shapes. FIG. 1, reference number 13 shows the typical output of the circuit in the forms of current through the coil and voltage across the coil. The low

| Figure # | Title | Reference Numerals |
|---|---|---|
| 1 | Embodiment #1: Proof of Concept | 11-Original circuit<br>12-First coil, wound on a wicker collapsible shelf.<br>13-Traces showing class-A common-emitter operation of the amplifier |
| 2 | Embodiment #2: Astable Multivibrator | 21-Astable Multivibrator circuit<br>22-Coil winding jig built out of necessity because too many people wanted a device.<br>23-Current traces showing how the device capitalized on the circuit design to alternately power "flux up and "flux down" coils. |
| 3 | Embodiment #3: TTL Timer-driven Transistor H-Bridge | 31-The 555-based circuit with the new BJT-transistor-based circuit.<br>32-Voltage and current traces showing how a single logical pin out of the 555 timer reversed the current in the coil to maximum levels in either direction. |
| 4 | Embodiment #4: Attiny85 Micro-Processor Driven MOSFET H-Bridge | 41-Atttiny85-based circuit driving four complementary MOSFETs.<br>42-Voltage and current traces showing how the two digital outputs from the microprocessor alternately reversed the coil current to the flux up or flux down direction. |
| 5 | Embodiment #5: ATmega328P Micro-Processor Driven MOSFET H-Bridge | 51-ATmega328P processor based mini microcontroller with more GPIO pins allowing the processor to monitor the output to the coil directly, and to shut power off to the driver circuit if a coil circuit malfunction occurs.<br>52-O-Scope screen capture to show coil current wave-shaping in real time. |
| 6 | Present Embodiment of Coil | N/A |
| 7 | Typical Embodiment of Human Proportions | N/A |
| 8 | Typical Gauss Developed By Coil, Placed Top/Bottom of Pillow | N/A |
| 9 | Current Embodiment being produced: Coil and Electronic Module | 91: Coil, 92: Cable to Electronic Module, 93: Electronic Module, 94: Indicator Ring, 95: Pushbutton, 96: USB Power Cable with TYPE A plug. |
| 10 | Drawing to Vendor | N/A |

The device produces a varying magnetic field of a specific frequency, in the vicinity of the head while sleeping where the entire head is exposed to the variance, not just one region of the head and where the strength of the magnetic field is on the order of magnitude of Earth's own magnetic field. That being said, the shape of the coils, the electrical parameters of the components, and the enclosures used to house the electronics are somewhat arbitrary and the inventor used what he had on hand to achieve the design objective. For instance, the coil may be circular or it may be rectangular or oval. The component of magnetic flux vertical to the plane of the coil in each case will suffice to achieve the design objective. Different transistors and microprocessors were used and different parts were selected because variances in discrete components values necessitated adjustments to achieve the desired frequency. Parts typically vary from inductance of the coil is evidenced by the phase relationship between the current and the voltage.

FIG. 2, reference number 21 shows a typical stable multivibrator approach to generating the magnetic flux. The inventor shifted to using magnet wire and developed a winding jig (FIG. 2, reference number 22) to speed up coil-making. Each unit required two coils, powered alternately by Q1 and Q2 to achieve the desired bi-directional variance in the flux. FIG. 2, reference number 22 shows the current through each coil, in phase relationship to each other.

FIG. 3, reference number 31 shows the inventor shifting to a 555-timer-driven approach and a transistorized H-bridge configuration for providing current to the coil. This further sped up assembling units for testers, all of whom approached the inventor based on what others were expressing about their successes with the invention. Adjusting the 10K_var resistor allowed the inventor to quickly adjust frequency to the desired value, and the h-bridge circuit enabled the use of half the amount of copper wire. FIG. 3, reference number 32 shows the direction of current through the coil in phase relationship to the output of the 555 timer. The desired bi-directional variance in the flux was achieved.

FIG. 4, reference number 41 shows the inventor shifting to micro-processor driven output to the h-bridge, and a shift from BJTs to MOSFETs. This achieved several design objectives including providing an easy means of connecting power as the microprocessor contained a built-in micro-USB receptacle. It allowed for an indicator to more readily communicate working status to the user. It allowed for a software adjustment versus a hardware adjustment to establish the desired frequency. It allowed for more consistent levels of current to be provided to the coil across multiple units that were built for testers. FIG. 4, reference number 42 shows how the two output signals from the microprocessor alternately enabled each half of the H-bridge to provide the bidirectional current through the coil.

FIG. 5, reference number 51 shows the inventor shifting to a better microprocessor to allow for mass production. This removed the need for calibration as the processor produced the desired frequency within the desired tolerance of +/−0.02 Hz. It also allowed for the microprocessor to monitor the output of the h-bridge and shut the unit down and alert the user if there is a problem with the unit. FIG. 5, reference number 52 is the output of the calibrated o-scope the inventor used. Trace 1 and trace 2 are each side of the coil's voltage in reference to ground and trace M is the mathematical difference between the two to show the net voltage across the coil (and consequently the direction of the current through the coil).

FIG. 6 is an embodiment of the coil of the present invention.

FIG. 7 shows female and male Man-System Integration Standards to provide a frame of reference for establishing the size of the coil and its magnetic strength.

FIG. 8 shows typical propagation of magnetic flux vertically up through the center-line of the coil (right axis), and horizontally out from the side of the coil (left axis).

Figure 9:
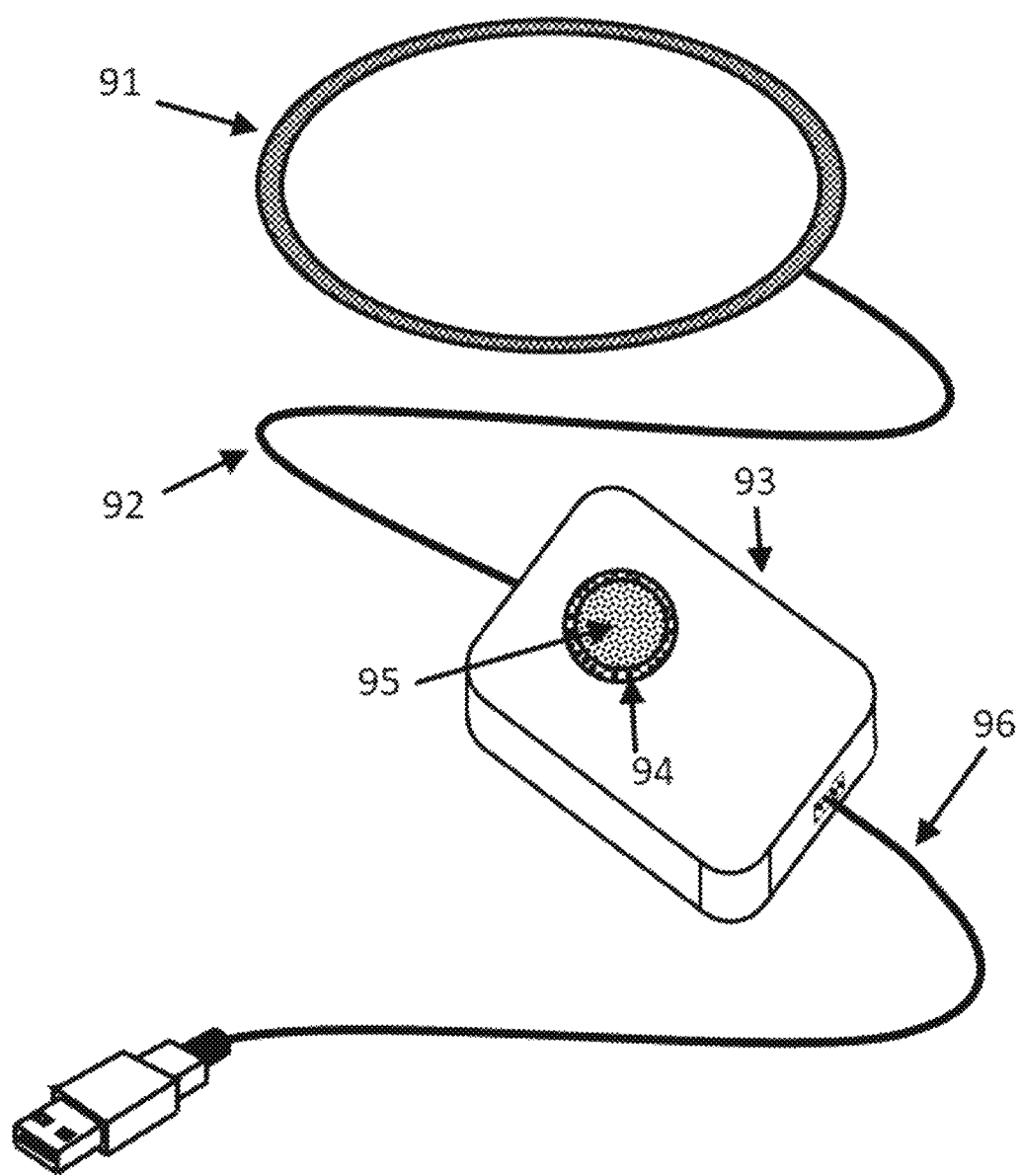
FIG. 9 is a schematic of an embodiment of the coil of an embodiment of the invention.

FIG. 9 shows an embodiment of the coil of the present invention. There is a coil (reference #91) that gets placed by the user as desired. The coil is plugged into the electronic module enclosure (reference #93) via a cable (reference #92). A standard micro-USB cable (reference #96) plugs into the other side to power the unit from any USB type female plug. The indicator ring (reference #94) lets the user know it is functioning properly. The push button (reference #95), can be used to energize or de-energize the coil if desired. Pressing the button is not required to operate the unit. Multiple lengths and enclosure dimensions are usable so it is a moot point to include them.

Figure 10:
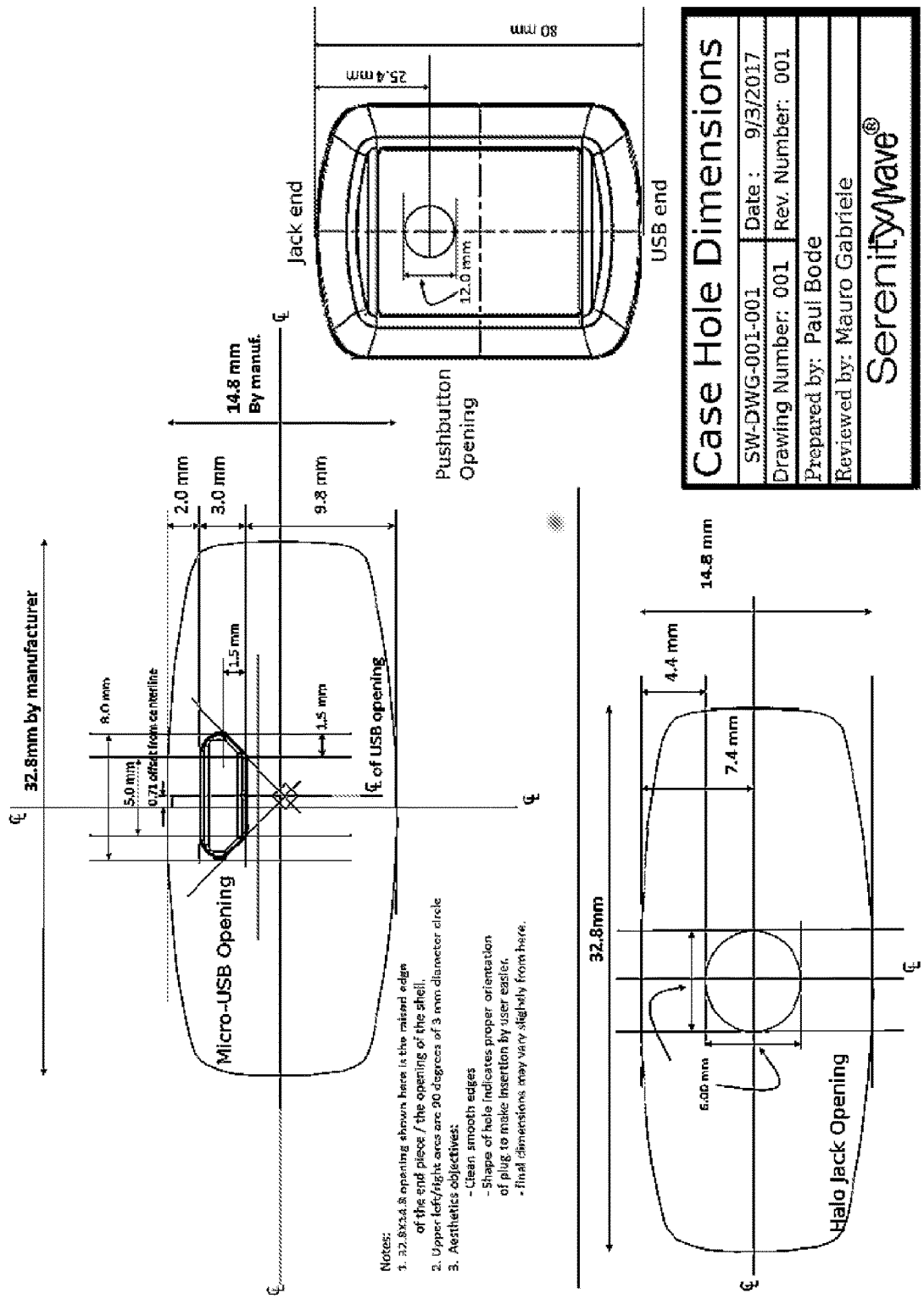
FIG. 10 is a schematic of an embodiment of the coil of an embodiment of the invention.

FIG. 10 is provided for reference of a typical enclosure.

Embodiments

The narrative progression through the embodiments provides for a detailed description of, and an understanding of the operation, of the invention.

First Embodiment

FIG. 1: Proof of Concept

At the conclusion of the inventor's research, the inventor purchased an "Arbitrary Waveform Generator" capable of producing any wave shape (not just square, sine or triangle). The output was set to 7.83 Hz with a voltage amplitude and DC offset suitable to drive a class-A transistorized amplifier. A single transistor, configured in a common-emitter mode was used to drive a coil placed under the pillow. The voltages can be adjusted on a per-transistor basis making any transistor suitable for carrying 250 mA acceptable to use. FIG. 1, reference number 11, depicts the circuit conceptually for the selected transistor. Values would change for different transistors, but circuit operation would be the same.

The coil was made from stranded 20-gauge wire in a plastic sheath and was approximately 100 turns, air core, the approximate size of the pillow. This is depicted in FIG. 1, reference number 12. A 25-ohm resistor was placed in series with it to limit current through the coil from a 12-volt power supply so as to control the strength of the magnetic field. FIG. 1, reference number 13 shows the relationship between signal voltage and coil current and voltage. The circuit used less than 250 mA to establish the desired level of flux of +/−0.5 Gauss (the approximate strength of Earth's magnetic flux).

With only a 12V power supply available initially, this circuit made the inventor realize he could capitalize on the ubiquitous 5V USB wall charger for future power as the coil only needed 4 volts/220 mA to produce the desired flux, as measured with a high-end smart phone. Subsequently the inventor used a magnetometer (listed on FIG. 8).

Second Embodiment

FIG. 2—Astable Multivibrator

A second embodiment was created consisting of an astable multivibrator circuit (FIG. 2, reference number 21) using two transistors and hand-selected components to account for variances between actual values and recorded component values, as these affect frequencies of operation. The output of each transistor was fed to one side of a hand-made center-tap air core coil. The polarity of the coils was set up such that they would oppose each other. Given that they were never on at the same time they provided for a full-wave magnetic flux signal that alternately aided, then opposed, the Earth's magnetic field. Typical current traces for the respective coils are shown in FIG. 2, reference number 23. The coil was bulky and unsuitable for permanent use, being made of 18-5 conductor. This circuit also eliminated the need for a separate signal generator.

Coils were then made from 26-gauge enamel coated magnet wire, center-tapped, initially wound on a 5-gallon pail lid, but then wound using a jig (FIG. 2, reference number 22). The larger dowel was used to spin the platform as wire was fed on to it. Testers of the device noticed improved sleep the first night they used the device. Many reported other physical or emotional improvements as well, typically becoming self-aware of them within a two-week period.

Third Embodiment

FIG. 3—TTL Timer Driver Transistor H-Bridge

In the second embodiment, there were no clamping diodes and the inductive kick degraded the capacitors allowing the frequency to drift. Consequently, the oscillation was shifted to the ubiquitous 555 IC timer chip. The circuit is depicted in FIG. 3, reference number 31. This shielded the RC time circuit from the inductive kick and also allowed for a more adjustable frequency control using adjustable resistors, with the frequency verified on a calibrated TekTronix o-scope, after a quick simple adjustment on a variable resistor. The device was quicker because it provided a means of rapidly adjusting circuit frequency without having to cherry-pick components to ensure the correct frequency.

The inventor used transistors to electronically flip the coil which made it easy for him to halve the amount of copper needed in the coils to produce the same field. The inventor no longer needed two halves of a coil to operate independently. This allowed for a thinner coil with less copper, but still stiff Quicker coil construction also helped speed up assembly. This used a single coil with no center-tap, with half the number of turns of the center-tapped coil.

In the third embodiment, the power supply was shifted to the standardized 5-volt USB power system and the output resistors were eliminated as they were no longer required. This made it cheaper and easier to power. FIG. 3, reference number 32 shows how the single digital output of the 555 timer was used to alternate the current in the coil in either direction.

In practice, an LED powered off of the output coil was used as an indicator to show that it was working.

Fourth Embodiment

FIG. 4—Attiny85 Microprocessor-Driven MOSFET H-Bridge

The output indicator confused people as it was blinking so rapidly so the inventor needed a solution that allowed him to disconnect the indicator from the coil function.

At this point the inventor shifted to a commercially available microprocessor with sufficient input/output functions to control the coil, and provide indication. It was a Attiny85 processor based mini microcontroller with 4 GPIO pins. Unlike some previous art, this required no special crystal.

It simplified the component selection process as the processor now controlled the oscillation, not an RC time constant made of discrete components. The circuit can be seen at FIG. 4, reference number 41.

The inventor also shifted from bi-polar transistors to complementary N-channel and P-channel MOS-FETs to drive the coil. These had lower on-state resistances and dissipated less heat, making the units more reliable. They also had built-in clamping diodes which made for better circuit component protection and reduces ringing in the coils as it changed state.

In this embodiment, the inventor shifted from permanently affixed Halo coils, to coils that were wired to standard audio aux cables with standard male 3/8" stereo plug on the other end. This plugs into a standard 3/8" female jack on the electronic module.

The inventor still had to calibrate each unit using the o-scope because of variances in the ceramic oscillator circuit. This is accomplished in the timing of the output of the microprocessor. The inventor also experienced occasional heating because of a problem with the manufacturing of the MOSFETs. The current trace for the coil can be seen in relation to the output of the microprocessor in FIG. 4, reference number 42. Two outputs from the microprocessor each drove one direction of the Halo's magnetic flux, alternately.

Fifth Embodiment

FIG. 5—Atmega328P Micro-Processor Driven MOSFET H-Bridge

To correct the need for calibration, the inventor upgraded to a better CPU with a better clock. Now each unit is within tolerance without the need for adjustment. The circuit can be seen in FIG. 5, reference number 51. The inventor shifted to a ATmega328P processor based mini microcontroller with more GPIO pins allowing the processor to monitor the output to the coil directly, and to shut power off to the driver circuit if a coil circuit malfunction occurs. This embodiment employs wave-shaping via Pin 6 duty cycle, R7 and C2 RC time constant to silence the flexible coil. The unit produces a continuous gentle wave, not pulsed as many other devices operate (see FIG. 5, reference number 52). Unlike other approaches, it is not purely a digital wave where it is on or off, nor is it a continuous voltage, switched in polarity. The production unit slopes the leading and trailing edge of the wave form, eliminating any sound produced as is found in many other devices. Traces on FIG. 5, reference number 52 are directly off of the oscilloscope. They show both sides of coil to ground (1, 2—top two traces), and their difference (M—bottom trace), the effective voltage across the coil. This serves to illustrate the wave shaping. The bottom trace on FIG. 5, reference number 52 shows the wave form of voltage (and consequently its current given the low inductance of the Halo).

The inventor also took the extra GPIO microprocessor inputs that were now available and monitor the output to the coil every time it changes state. If any of the output MOSFETs fail (short or open or fail to change state for any reason), the unit shuts down automatically in less than a second and the indicator shifts to a mode to let the user know they need to reset the unit.

A flexible coil was developed. The turns of the magnet wire are not rigidly bonded to each other. One version was over-molded with a silicone compound. Another version has a helical wrap holding the turns in place. This allows for comfort; the coil can be flexed at night and still produce the magnetic field. This also allows the coil to be folded in on itself two or three times to make for easier packing and for travel. The operation and use of the coil allows it to be unplugged from the electronic module. Currently, the coil plugs into the electronic module using a standard aux jack configuration. Other approaches for coil construction, stiffness and connecting have also been used. FIG. 6 shows the salient dimensions of the coil currently being manufactured. FIG. 10 is a copy of the electronics enclosure drawing.

The device is powered by a generic micro-USB power cord and USB charger. An advantage of the device is because it draws less than 500 mA and uses a standard USB charger and all USB chargers are rated for 500 mA or greater as part of the USB standard, a user can easily buy a second charger. The present version of the device is designed to power two Halo coils, for couples. The second Halo is presently referred to as the Honey Halo.

Summary of Embodiments

The patent focuses on (1) the nature of the coil design, flexibility and physical size to create the required gradient in the area of the head of the user (2) the use of a single natural frequency as designed by Earth exposing us to this frequency, (3) the strength of the field being of the order of magnitude of the Earth's own field, (4) the simplicity of operation and use, (5) not requiring any electrodes, pads or head bands to be attached to the person or animal using the device, and (6) the application using no obtrusive hardware requirements. The methods for design, operation and use of Earth's natural magnetic resonance for sleep enhancement are singularly unique herein.

The device has evolved from simple transistorized circuits, through an IC-based circuit, to a simple micro-processor-based circuit, to a more sophisticated micro-processor controlled coil.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

The invention claimed is:

1. A varying magnetic field generating system comprising:
    a flexible air-core coil consisting of only wire, an outer soft cover, with only air in the center of the coil, the flexible air-core coil configured to create a varying magnetic field through the head of a user;
    an electronic module configured to operate below 500 mA at 5V and to power the flexible air-core coil at a frequency of 7.83 Hz+/−0.5 Hz;
    wherein the flexible air-core coil is configured to be inserted into a pillow case or beneath a pillow of the user,
    wherein the flexible air-core coil produces a low-gradient uniform flux through the entire head of the user,
    wherein the frequency of flux produced by the coil is 7.83 Hz+/−0.5 Hz;
    wherein amplitude in gauss variance across the head of the user averages between 0 and 1 Gauss,
    wherein the flexible air-core coil is configured such that an inner diameter of the coil is greater than 95% of an outer diameter of the coil, with the inner diameter dimensioned to be greater than 13 inches, larger than that of the head of the user;
    wherein the coil is configured to flex with the pillow allowing for comfort during use or for folding during travel; and
    wherein the system enhances quality of sleep of the user.

2. The system of claim 1, wherein the inner diameter of the flexible air-core coil is larger than a human head in any cross-section.

3. The system of claim 1, wherein the flexible air-core coil is configured to be placed over the head of the user and worn around the neck of the user.

4. The system of claim 1, wherein the system produces the gauss variance in the magnetic field in the area of the head of the user, and not the whole body.

5. The system of claim 1, wherein the system enhances sleep exclusively with the application of the varying magnetic field without the use of any other therapeutic means.

6. The system of claim 1, wherein the magnetic field varies at a single frequency.

7. The system of claim 1, wherein the system is configured to work without direct contact of any of its components with the user or being placed on or attached to the body, while the user is sleeping.

8. The system of claim 1, wherein the electronic module only requires a simple, single indicator light to inform the user that the module is operating correctly or not, thereby communicating multiple states of operation to the user.

9. The system of claim 1, wherein the electronic module is configured to be powered using any standard USB port or power supply.

10. A method of assisting a user to sleep, the method comprising:
    providing a flexible air-core coil consisting of only wire, an outer soft cover, with only air in the center of the coil, the flexible air-core coil configured to create a varying magnetic field through the head of the user;
    providing an electronic module configured to operate below 500 mA at 5V and to power the flexible air-core coil at a frequency of 7.83 Hz+/−0.5 Hz;
    applying a low-gauss, low-frequency magnetic field around the head of the user via the flexible air-core coil while the user is asleep,
    wherein the flexible air-core coil is configured to be inserted into a pillow case or beneath a pillow of the user,
    wherein the flexible air-core coil produces a low-gradient uniform flux through the entire head of the user,
    wherein the frequency of flux produced by the coil is 7.83 Hz+1-0.5 Hz;
    wherein amplitude in gauss variance across the head of the user averages between 0 and 1 Gauss,
    wherein the flexible air-core coil is configured such that an inner diameter of the coil is greater than 95% of an outer diameter of the coil, with the inner diameter dimensioned to be greater than 13 inches, larger than that of the head of the user;
    wherein the coil is configured to flex with the pillow allowing for comfort during use or for folding during travel; and
    wherein the system promotes sleep and enhances quality of sleep of the user.

11. The method of claim 10, wherein the low-gauss, low-frequency magnetic field is generated as a wave.

12. The method of claim 10, wherein the magnetic field is directed towards a vicinity of the head of the user.

* * * * *